United States Patent
Ohta et al.

[11] Patent Number: 6,127,152
[45] Date of Patent: Oct. 3, 2000

[54] PROCESS FOR PRODUCING NUCLEOSIDE DERIVATIVES

[75] Inventors: Hiromichi Ohta, Tokyo; Takeshi Sugai, Yokohama; Takeshi Ishii, Toyonaka; Satoshi Mitsuda, Takarazuka, all of Japan

[73] Assignee: Sumitomo Chemical Company, Limited, Osaka, Japan

[21] Appl. No.: 09/127,124

[22] Filed: Jul. 30, 1998

[30] Foreign Application Priority Data

Jul. 31, 1997 [JP] Japan ................................ 9-206149

[51] Int. Cl.$^7$ ...................................................... C12P 19/38
[52] U.S. Cl. ................. 435/87; 435/89; 435/85; 435/72; 435/197; 435/84
[58] Field of Search .................. 435/87, 89, 85, 435/72, 197, 84

[56] References Cited

PUBLICATIONS

Enzymatic Regioselective Deacylation of 2′,3′,5′–Tri–O–Acylribo–Nucleosides: Enzymatic Synthesis of 2′,3′,–Di–o–Acylribonucleosides, Haribansh K. Singh et al., Tetrahedron Letter, vol. 34, pp. 5201–5204 (1993).

*Primary Examiner*—Francisco Prats
*Attorney, Agent, or Firm*—Birch, Stewart, Kolasch & Birch, LLP

[57] ABSTRACT

There is disclosed a process for producing a nucleoside derivative of the formula [I]:

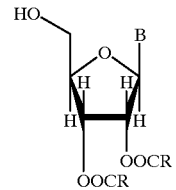

characterized by contacting 2′,3′,5′-O-triacylribonucleoside derivative of the formula [II]:

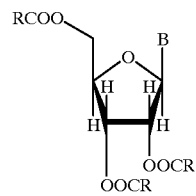

with an ester hydrolase:

(i) capable of regio-selectively deacylating the acyl group at 5′-O-position in the formula [II] above, and
(ii) having an amino acid sequence encoded by a gene which hybridizes to a nucleotide sequence encoding an amino acid sequence of SEQ ID NO:1.

4 Claims, No Drawings

PROCESS FOR PRODUCING NUCLEOSIDE DERIVATIVES

FIELD OF THE INVENTION

The present invention relates to a process for producing nucleoside derivatives.

DESCRIPTION OF THE RELATED ART

2',3'-O-diacrylribonucleosides are useful as intermediates for the synthesis of oligosaccharides such as sialic acid-containing oligosaccharides that are useful for pharmaceutical preparations effective for prophylaxis of inflammation, inhibition of metastasis of cancer, prevention of viral infection and so on.

Therefore, a convenient process for producing 2',3'-O-diacylribonucleosides derivative has been desired.

SUMMARY OF THE INVENTION

An object of the invention is to provide:
a process for producing a nucleoside derivative of the formula [I]:

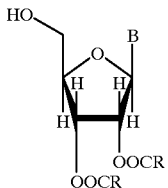

wherein B represents a purine base in which an amino group may be protected or a pyrimidine base in which an amino group may be protected, and R represents an alkyl group having 1–20 carbon atoms,
which comprises contacting 2',3',5'-O-triacylribonucleoside derivative of the formula [II]:

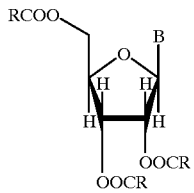

wherein R and B are the same as defined above, with an ester hydrolase:
(i) capable of regio-selectively deacylating the acyl group at 5'-O-position in the formula [II] above, and
(ii) having an amino acid sequence encoded by a gene which hybridizes to a nucleotide sequence encoding an amino acid sequence of SEQ ID NO:1.

DESCRIPTION OF THE PREFERRED EMBODIMENT

The present invention is described below in detail. In the present process, the purine base in which an amino group may be protected for B in formula [I] or [II] includes adenine, guanine, xanthine, hypoxanthine and the like.

The pyrimidine base in which an amino group may be protected for B in formula [I] or [II] includes cytosine, thymine, uracil, 5-methylcytosine, 5-oxymethylcytosine and the like.

The amino group of the pyrimidine or purine may be protected by an acyl group such as an acetyl group, chloroacetyl, dichloroacetyl, trichloroacetyl, trifluoroacetyl, p-methoxybenzoyl, benzoyl, isobutyryl, 2-methylbutyryl group, all of which and other protectives groups can be used according to a conventional method as disclosed in "Protective Groups in Organic Synthesis", Theodora W. Greene, Published by John Wiley & Sons, Inc. (1981), the whole content of which is incorporated herein by reference.

The alkyl group having 1–20 carbon atoms for R in formula [I] or [II] includes methyl group, ethyl group, propyl group, isopropyl group, isobutyl group, butyl group, t-butyl group, wherein "t" means "tertiary", and the same shall apply hereinafter, amyl group, isoamyl group, t-amyl group, n-hexyl, n-octyl, n-nonyl, n-decyl,, n-undecyl, n-dodecyl, n-tridecyl, n-tetradecyl, n-pentadecyl, n-hexadecyl, n-heptadecyl, n-octadecyl, n-nonadecyl, n-Icosyl and the like.

The 2',3',5'-O-triacylribonucleoside derivative of the formula [II] can be prepared from the corresponding ribonucleoside according to a known method, for example, a method described in Tetrahedron Letters, No. 9, p. 733 (1969).

For Example, a 2',3',5'-O-triacylribonucleoside derivative can be produced by reacting a carboxylic acid anhydride such as acetic anhydride and the like or a carboxylic acid halide such as acetyl chloride and the like with a ribonucleoside dissolved in pyridine.

The carboxylic acid anhydride used here includes, beside acetic anhydride, propionic anhydride, butyric anhydride, valeric anhydride and the like, and the carboxylic acid halide includes, beside acetyl chloride, propionyl chloride, butyryl chloride, acetyl bromide, propionyl bromide, butyryl bromide and the like.

Thus produced 2',3',5'-O-triacylribonucleoside derivative can be isolated by a conventional post-treatment such as removal of the solvent by distillation, separation by extraction, chromatography or the like.

Specific examples of the 2',3',5'-O-triacylribonucleoside derivative of the formula [II] include:
  2',3',5'-O,$N^4$-tetraacetylcytidine,
  2',3',5'-O-triacetylcytidine,
  2',3',5'-O-triacetyl-5-methylcytidine,
  2',3',5'-O-triacetyladenosine,
  2',3',5'-O-triacetylguanosine,
  2',3',5'-O,$N^4$-tetraacetylguanosine,
  2',3',5'-O-triacetylinosine,
  2',3',5'-O-triacetyluridine,
  2',3',5'-O,$N^4$-tetrapropionylcytidine,
  2',3',5'-O-tripropionyluridine and
  2',3',5'-O-tributyryladenosine.

The present process uses an ester hydrolase (hereinafter referred to as "the present ester hydrolase"):
(i) capable of regio-selectively deacylating the acyl group at 5'-O-position in the formula [II] above, and
(ii) having an amino acid sequence encoded by a gene which hybridizes to a nucleotide sequence encoding an amino acid sequence of SEQ ID NO:1.

The ester hydrolase may be derived from an animal such as pig, human and the like, or derived from a plant such as castor and the like, or derived from a microorganism belonging to Aspergillus, Candida, Fusarium, Geotrichum, Mucol, Nocardia, Penicillium, Rhizopus, Saccharomyces, Achromobacter, Acinetobacter, Alcaligenes, Chromobacterium, Escherichia, Pseudomonas, Sphingomonas, Bacillus, Burkholderia, Moraxella, Lactobacillus, Staphylococcus, Serratia, Yarrowia and the like.

In addition, it may be an ester hydrolase produced by a transformant into which a gene for such ester hydrolase is introduced. From the viewpoint of manufacturing cost, enzymes produced by microorganisms are preferred.

Examples of the present ester hydrolase include:

an ester hydrolase having an amino acid sequence which has homology of 90% or more with an amino acid sequence of SEQ ID NO:1 and capable of regioselectively deacylating an acyl group at 5'-O-position of a 2',3',5'-O-triacylribonucleoside derivative of the formula [II], an ester hydrolase having an amino acid sequence in which one or several amino acids are added to, deleted from, modified in or substituted in an amino acid sequence of SEQ ID NO:1 and capable of regioselectively deacylating anacyl group at 5'-O-position of a 2',3',5'-O-triacylribonucleoside derivative of the formula [II]: and an ester hydrolase having an amino acid sequence of SEQ ID NO:1 and the like.

The term "hybridize" herein refers to the fact that a double-stranded form is produced between a single-stranded DNA and a single-stranded DNA or a single-stranded RNA that is complementary to the former-most when a double-stranded DNA, a single-stranded DNA or/and a single-stranded RNA are mixed and treated for dissociation from a double-stranded DNA to a single-stranded DNA by a heat-treatment under conditions, for example at 95° C. for 1 minute, and then treated for radiation of heat under conditions of allowing to stand at room temperature for 1 minute, or treated for dissociation from a double-stranded DNA to a single-stranded DNA by alkali treatment under conditions of 0.5 M NaOH and 1.5 M NaCl and then treated for neutralization under conditions of 0.5 M Tris.HCl (pH 7.0) and 3.0 M NaCl.

The term "a gene which hybridizes" refers to a gene having such a complementarity. Specific examples include a gene having a base sequence encoding an amino acid sequence which has a homology of 90% or more with an amino acid sequence of SEQ ID NO:1.

A microorganism (a strain: E. coli JM109/pAL108) which produces an ester hydrolase having an amino acid sequence of SEQ ID NO:1 has been deposited to the National Institute of Bioscience and Human-Technology Agency of Industrial Science and Technology, Ministry of International Trade and Industry, under the Budapest Treaty with an accession number of FERM-BP5739 (date of receipt: Nov. 7, 1996).

Said microorganism can be cultured in various media which are used in routine cultivation of general microorganisms and which contain carbon sources, nitrogen sources with optional organic or inorganic salts and so on.

The carbon sources include glucose, glycerol, dextrin, sucrose, organic acids, animal or plant oils, molasses and the like.

The nitrogen sources include organic or inorganic nitrogen sources and the like such as meat extract, peptone, yeast extract, malt extract, soybean flour, corn steep liquor (Corn Steep Liquor), cotton seed flour, dry yeast, casamino acid, sodium nitrate, urea and the like.

The organic or inorganic salts include chlorides, sulfates, acetates, carbonates and phosphates of potassium, sodium, magnesium, iron, manganese, cobalt, zinc and so on, specifically, sodium chloride, potassium chloride, magnesium sulfate, ferrous sulfate, manganese sulfate, cobalt chloride, zinc sulfate, copper sulfate, sodium acetate, calcium carbonate, sodium carbonate, potassium dihydrogen phosphate, dipotassium hydrogen phosphate and the like.

The cultivation can be performed according to a conventional method for general microorganism, and anyone of solid culture, liquid culture (shaking culture in test tube, reciprocal shaking culture, jar fermenter (Jar Fermenter) culture, fermentation tank culture and the like) is possible. When a jar fermenter is used, it is necessary to introduce sterile air, and usually used aeration condition is about 0.1—about 2 times the volume of culture/minute.

The culturing conditions may adequately be set within a range in which the microorganism can grow, and it is preferred that the culture is conducted, for example, at a culture temperature in a range of about 15° C. to about 40° C. and a pH of medium from about 6 to about 8. While the culture period varies depending on various culture conditions, about 1 to about 5 days are usually desirable.

The present ester hydrolase can be utilized in the reaction in the form of microorganisms or cells containing it or be utilized in the reaction in the form of a crude enzyme, purified enzyme or the like separated from said culture or a tissue containing said ester hydrolase. Methods for such separation include conventional methods in which microorganisms, cells, tissues or the like are crushed by, for example, ultrasonic treatment, trituration with glass beads or alumina, treatment with French press, treatment with enzyme such as lysozyme or the like, treatment with Waring blender and the like, and the crushed product is fractionated by salting out with ammonium sulfate, precipitation with organic solvent or organic polymer such as polyethylene glycol or the like, various chromatographies such as ion-exchange chromatography, hydrophobic chromatography, gel filtration chromatography, affinity chromatography and the like, electrophoresis and so on. These methods can be combined, if necessary.

In addition, the present ester hydrolase can be used in the easily separable insolubilized form. Insolubilization of the enzyme can be accomplished by immobilizing the enzyme by immobilizing methods such as the carrier binding method in which said hydrolase is bound to a carrier by covalent bond, ion bond, adsorption or the like, entrapment method in which said hydrolase is entrapped in a meshwork of high polymer and the like.

In the process of the present invention, the present ester hydrolase is contacted with the 2',3', 5'-O-triacylribonucleoside derivative of the formula [II], for example, about 15° C. to about 60° C., preferably about 25° C. to about 40° C.

The reaction pH is, for example, about 4 to about 9, preferably about 6 to about 8, and it is preferred to use a pH buffering solution in order to keep the pH value within a suitable range.

As the pH buffering solution can be used a pH buffering solution consisting of an aqueous solution of an inorganic salt such as a phosphate buffer or a pH buffering solution consisting of an aqueous solution of an organic base such as trishydroxymethylaminomethane (Tris).HCl buffer and the like.

The reaction period is not specifically limited and is usually, for example, about 5 minutes to about 96 hours. In addition, in order to improve solubility of substrate in the reaction solution, a hydrophilic organic solvent that does not inhibit the enzymatic activity can be added to the reaction solution.

The hydrophilic organic solvent used for such purpose includes, for example, lower alcohols such as ethyl alcohol, propyl alcohol and the like or dimethylformamide or dioxane or dimethylsulfoxide and the like.

After completion of the reaction, 2',3'-O-diacylribonucleoside derivative of the formula [I] can be obtained from the reaction solution, by a conventional procedure including salting out, precipitation by solvent, column chromatography and the like.

Specifically, for example, a residue obtainable by evaporating solvent from the reaction solution under reduced pressure can be transferred to silica gel thin layer chromatography to separate the desired product of the reaction.

Examples of the 2',3'-O-diacylribonucleoside derivatives of the formula [I] thus produced by the present process include the following compounds.

2',3'-O-diacylribonucleoside derivative of the formula [I]:

2',3'-O,$N^4$-triacetylcytidine,

2',3'-O-diacetylcytidine,

2',3'-O-diacetyl-5-methylcytidine,

2',3'-O-diacetyladenosine,

2',3'-O-diacetylguanosine,

2',3'-O,$N^4$-triacetylguanosine,

2',3'-O-diacetylinosine,

2',3'-O-diacetyluridine,

2',3'-O,$N^4$-tripropionylcytidine,

2',3'-O-dipropionyluridine, and

2',3'-O-dibutyryladenosine.

The present invention will be described in more detail by means of Examples, but the present invention is not limited by these Examples.

EXAMPLE 1

Into a test tube containing 8 ml of a sterilized liquid medium (an aqueous solution containing 10 g/l Bacto Tripton (manufactured by Difco); 5 g/l Bacto Yeast Extract (manufactured by Difco); 5 g/l NaCl; 1 mM isopropyl-β-D-thiogalactopyraniside; 50 μg/ml Ampicillin) was inoculated a strain *E. coli* JM109/pAL108 (Accession number of microorganism: FERM BP-5739) and cultured under reciprocal shaking at 37° C. for 8 hours to give a culture solution as a pre-culture. Subsequently, into a 3 liter small fermenter containing 1.5 liter of a sterile medium having the same composition was inoculated 7.5 ml of the pre-culture and the medium was stirred at 37° C. at 500 rpm while introducing sterile air at a rate of 0.75 liter per minute. The culture solution obtained after 15 hours was centrifuged to collect cells. The obtained cells were suspended in 50 ml of 100 mM phosphate buffer (pH 7.0) and crushed by ultrasonic treatment. The obtained crushed-cell suspension was centrifuged to give a supernatant as a cell-free extract. To this cell-free extract was dissolved ammonium sulfate to a concentration of 80%, and then the mixture was centrifuged and precipitates were collected. The collected precipitates were suspended in 50 ml of 100 mM phosphate buffer (pH 7.0) and subjected to desalinization treatment by dialysis to give a crude enzyme solution. The obtained crude enzyme solution was freeze-dried to give a powdery crude enzyme sample of the ester hydrolase.

Subsequently, 9 g of 2',3',5'-O,$N^4$-tetraacetylcytidine was dissolved in 9 g of ethyl alcohol in a glass container, 90 ml of 0.2% aqueous Triton X100™ solution was added thereto, 270 ml of 0.2 M concentration phosphate buffer (pH 7.2) was further added, and the mixture was incubated at 30° C. while stirring with a magnet rotor. To this was added 20 mg of the above-described crude enzyme sample of the ester hydrolase to commence the enzymatic reaction. 6 Hours after the commencement of the enzymatic reaction, 90 g of anhydrous sodium sulfate was added to and dissolved in the reaction solution, upon which the product precipitated. The precipitates were collected by filtration and air-dried. The obtained solid was charged onto a column packed with silica gel, eluted with a mixed solvent of ethyl acetate and ethyl alcohol (1:1 in the volume ratio), and the solvent was stripped off from the obtained eluate under reduced pressure to give 6 g of the product. The product obtained here was confirmed to be an almost pure 2',3'-O,$N^4$-triacetylcytidine by $^1$H-NMR measurement in heavy water.

EXAMPLE 2

In a 100 ml glass container, 0.37 g of 2',3',5'-O-triacetyluridine was dissolved in 0.5 g of ethyl alcohol, 5 ml of 0.2% aqueous Triton X100™ solution was added thereto, 15 ml of 0.2 M concentration phosphate buffer (pH 7.2) was further added, and the mixture was incubated at 30° C. while stirring with a magnet rotor. To this was added 3 mg of the crude enzyme sample of the ester hydrolase prepared in Example 1 to commence the enzymatic reaction. 6 Hours after the commencement of the enzymatic reaction, 5 g of anhydrous sodium sulfate was added to and dissolved in the reaction solution, and the solvent was stripped off. The obtained solid was extracted with 100 ml of ethyl acetate and the solvent was stripped off from the extract under reduced pressure to give 0.32 g of the product. The product obtained here was confirmed to be an almost pure 2',3'-O-diacetyluridine by $^1$H-NMR measurement in heavy water.

What is claimed is:

1. A process for producing a nucleoside derivative of the formula (I):

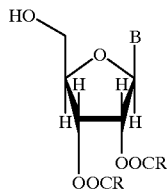
(I)

wherein B represents a purine base in which an amino group may be protected or a pyrimidine base in which an amino group may be protected, and R represents an alkyl group having 1–20 carbon atoms, which comprises contacting 2',3',5'-O-triacylribonucleoside derivative of the formula (II):

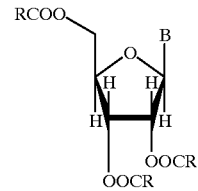
(II)

wherein R and B are defined above, with an ester hydrolase:
 (i) capable of regio-selectively deacylating the acyl group at 5'-O-position in the formula (II) above, and
 (ii) having an amino acid sequence of SEQ ID NO:1 or an amino acid sequence in which one or several amino acids are added to, deleted from, modified in or substituted in the amino acid sequence of SEQ ID NO:1 that has at least 90% sequence identity to SEQ ID NO:1.

2. The process according to claim 1, wherein R is a methyl group.

3. The process according to claim 1, wherein B is uridine or cytidine.

4. The process according to any one of claims 1–3, wherein the amino acid sequence of the ester hydrolase is the amino acid sequence of SEQ ID NO:1.

* * * * *

SEQUENCE LISTING

<160> NUMBER OF SEQ ID NOS: 1

<210> SEQ ID NO 1
<211> LENGTH: 393
<212> TYPE: PRT
<213> ORGANISM: Burkholderia cepacia

<400> SEQUENCE: 1

Met Ile Pro Asn Arg Ala Ser Ser Arg Gln Pro Ser Thr Asp Pro Ala
 1               5                  10                  15

Leu Ala Glu Arg Val Asp Ala Val Leu Ser Arg Gln Leu Glu Thr His
            20                  25                  30

```
Arg Leu Val Gly Val Val Leu Ile Ala Arg Asp Gly Glu Leu Val
         35                  40                  45

Tyr Arg Arg Ala Ala Gly Phe Ala Asp Arg Glu Ala Arg Thr Pro Met
 50                  55                  60

Arg Glu Asp Thr Leu Phe Arg Leu Ala Ser Val Thr Lys Pro Ile Val
 65                  70                  75                  80

Ser Ala Ala Ala Met Ala Leu Val Ala Gln His Lys Leu Ser Leu Asp
                 85                  90                  95

Asp Asp Val Thr Arg Trp Leu Pro Glu Phe Arg Pro Ala Leu Arg Asp
                100                 105                 110

Gly Ser Val Pro Val Ile Arg Val Arg His Leu Leu Thr His Thr Ala
             115                 120                 125

Gly Leu Gly Tyr Arg Phe Thr Glu Ala Asp Ala Thr Gly Pro Tyr Ala
             130                 135                 140

Arg Ala Gly Ala Ser Asp Gly Leu Asp Ala Ala Ser Ile Thr Leu Ala
145                 150                 155                 160

Glu Asn Leu Arg Arg Ile Ala Ser Val Pro Leu Gln Phe Ala Pro Gly
                165                 170                 175

Thr Gly Trp Asn Tyr Ser Leu Ser Ile Asp Val Val Gly Ala Leu Ile
             180                 185                 190

Glu Ala Val Ser Gly Leu Pro Leu Ala Asp Ala Ile Asp Thr Leu Val
             195                 200                 205

Leu Arg Pro Leu Gly Ala Arg Asp Thr Gly Phe Val Ala Arg Asp Ala
210                 215                 220

Ala Arg Leu Ala Thr Pro Tyr Val Asn Asp Thr Pro Gln Pro His Arg
225                 230                 235                 240

Leu Ala Glu Asn Glu Thr Val Pro Ile Phe Asp Gly Thr Val Gly Val
                245                 250                 255

Thr Tyr Ser Pro Ser Arg Ala Leu Asp Ala Asp Ala Phe Pro Ser Gly
                260                 265                 270

Gly Ala Gly Met Val Gly Thr Ala Gly Asp Val Leu Asn Leu Leu Asp
             275                 280                 285

Thr Leu Arg Ala Gly Gly Ser Leu Leu Pro Ala Asp Leu Val Asp
290                 295                 300

Glu Met Gly Arg Ala His Thr Gly Asn Leu Glu Leu Pro Asp Leu Pro
305                 310                 315                 320

Gly Ala Gly Phe Gly Ile Gly Phe Ser Val Leu Arg Asp Pro Leu Ala
                325                 330                 335

Ala Ala Ser Pro Glu Ser Val Gly Thr Trp Arg Trp Gly Gly Val Tyr
             340                 345                 350

Gly His Ser Trp Phe Val Asp Arg Ala Arg Gly Leu Thr Val Val Ser
             355                 360                 365

Leu Ser Asn Thr Leu Tyr Glu Gly Met Asn Gly Gln Tyr Thr Ile Asp
             370                 375                 380

Leu Arg Asp Ala Ile Tyr Gly Ala Gly
385                 390
```